United States Patent [19]

Clerici et al.

[11] Patent Number: 5,235,111
[45] Date of Patent: Aug. 10, 1993

[54] PROCESS FOR OXIDATING PARAFFINIC COMPOUNDS WITH OXYGEN

[75] Inventors: Mario G. Clerici, San Donato Milanese; Giuseppe Bellussi, Piacenza, both of Italy

[73] Assignees: Eniricherche S.p.A.; Shamprogetti S.p.A., both of Milan, Italy

[21] Appl. No.: 730,553

[22] Filed: Jul. 16, 1991

[30] Foreign Application Priority Data

Aug. 1, 1990 [IT] Italy ................. 21158 A/90

[51] Int. Cl.5 .......................................... C07C 45/33
[52] U.S. Cl. ........................... 568/399; 568/910; 568/910.5; 568/360
[58] Field of Search ............. 568/910, 910.5, 360, 568/399, 385

[56] References Cited

U.S. PATENT DOCUMENTS 4,480,135 10/1984 Esposito et al. ................. 568/385
4,803,187 2/1989 Lyons et al. ..................... 568/399
4,918,249 4/1990 Durante et al. .................. 568/399

FOREIGN PATENT DOCUMENTS 0226257 6/1987 European Pat. Off. ........... 502/239
0226258 6/1987 European Pat. Off. ........... 502/239
0266825 5/1988 European Pat. Off. ........... 502/239
0325053 7/1989 European Pat. Off. ........... 502/239
0376453 7/1990 European Pat. Off. ........... 568/385

*Primary Examiner*—James H. Reamer
*Attorney, Agent, or Firm*—Shea & Gould

[57] ABSTRACT

Process for oxidating paraffinic compounds into their corresponding alcoholic and/or ketonic derivatives, which process consists in causing said paraffins to react, at a temperature comprised within the range of from 0° C. to 100° C., preferably in an acidic medium, with a mixture of oxygen and hydrogen, in the presence of a catalyst on the basis of titanium-silicalite and of a noble metal and/or a derivative of such a metal.

25 Claims, No Drawings

PROCESS FOR OXIDATING PARAFFINIC COMPOUNDS WITH OXYGEN

The present invention relates to a process for oxidating paraffinic compounds into their corresponding alcoholic and/or ketonic derivatives, which process consists in causing said paraffins to react, at a temperature comprised within the range of from 0° C. to 100° C., preferably in an acidic environment, with a mixture of oxygen and hydrogen, in the presence of a catalyst on the basis of titanium-silicalite and a noble metal and/or derivative of such a noble metal.

Paraffins are known to be poorly reactive compounds, and, in general, for their functionalization, high temperatures or considerably strong reactants are necessary, such as, e.g., ozone, trifluoro-peracetic acid, chromic acid, permanganate: however, under such severe condition, that the selectivity values result to be unsatisfactory.

Also the oxidation of paraffinic compounds by means of hydrogen peroxide or of peroxy compounds in general, carried out in the presence of metal complexes as catalysts, has been disclosed. However, in general rather low yelds are obtained relatively to the peroxy reactant, owing to parallel reactions of decomposition into oxygen (J. T. Groves, G. A. Mc Clusky, J.A.C.S. page 859, 1976; J. B. Vincent et al., J.A.C.S. page 6898, 1988; R. H. Fish et al., J. Chem. Soc., Chem. Comm. page 1504, 1988).

The oxidation has been furthermore described of paraffins with hydrogen peroxide, at a temperature comprised within the range of from 0° C. to 100° C., by means of a process which uses, as the catalyst, a titanium-silicalite of formula

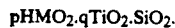

wherein M is a metal selected from aluminum, gallium, and iron, p is comprised within the range of from 0 to 0.05, with value zero being also allowed for p, and q is comprised within the range of from 0.0001 to 0.05, and preferably of from 0.01 to 0.025.

The latter process shows considerably high values of conversion and selectivity, relatively to both reactants, but is obviously penalized by the high cost of hydrogen peroxide. Therefore, from a financial viewpoint those processes are very interesting which makes it possible oxygen to be used as the oxidating agent for paraffins. In this regard, the oxidation of linear paraffins with oxygen is described, but it requires temperatures of round 150° C., and leads to the formation of a complex mixture of products containing, among others, acids, ketones, alcohols and peroxides, some products deriving from the fragmentation of the paraffinic compound (N. M. Emanuel, E. T. Denisov, Z. K. Maizus, Liquid Phase Oxidation of Hydrocarbons, Plenum Press, New York, 1987). The hard reaction conditions do not make it possible the selectivity of the process to be controlled, and the resulting complex mixture of products is difficult to be separated and used.

Furthermore, organometallic catalysts have been studied in the post, which are capable of oxidating paraffins in the presence of oxygen and of a suitable reducing agent. These catalysts have been defined "mono-oxygenase-like", in that this type of reaction is typical of mono-oxygenase enzymes.

In Mimoun et al., Tetrahedron, 31, page 177, (1975), the oxidation is described, e.g., of paraffins with oxygen in presence of a catalyst constituted by a metal in two different oxidation states, e.g., $Fe^{II/III}$, $Cu^{I/II}$, $Sn^{II/IV}$, $V^{III/IV}$, and in the presence of an organic compound as reducing agent, selected from ascorbic acid, hydrazobenzene or thiols: unfortunately, the yields obtained are very low and the reducing agent is consumed in stoichiometric amounts.

In Barton et al., J. Chem. Soc., Perkin Trans., 947 (1986), the reducing agent used is $Zn/H^+$ or $Fe/H^+$: in this case, a net consumption of iron or zinc is obtained, relatively to which the yields are lower than 5%.

In Tabushi et al., J. Am. Chem. Soc. 103, 7371, (1981) and Shilov, J. Chem. Soc., Chem. Comm., 731, (1987), the oxidation of paraffins with oxygen is catalyzed by porphyrinic complexes, possibly together with platinum as co-catalyst, whilst the reducing agent is hydrogen or zinc amalgam, in the presence of Methyl Viologen. The yields are very low, and the porphyrinic ligand is unstable to the oxidating agents.

In Herron and Tolmann, J. Am. Chem. Soc. 109, 2837, (1987), the reducing agent is hydrogen, the oxidation catalyst is $Fe^{II}$, the co-catalyst is palladium, and both are supported on a 5A zeolite, which should induce phenomena of shape selectivity: also in this case, the yields are low, and furthermore 95% of oxygen is directly transformed into water, without any usefulness for the reaction.

The present Applicants have surprisingly found now that it is possible to oxidate paraffinic compounds into their corresponding alcoholic and/or ketonic derivatives by means of a mixture of oxygen and hydrogen, with an oxidation catalyst of zeolitic nature and a noble metal, at low reaction temperatures.

Therefore, the object of the present invention is a process for the oxidation of paraffinic compounds into their corresponding alcoholic and/or ketonic derivatives, with a mixture of oxygen and hydrogen, by using a catalyst based on titanium-silicalite and a noble metal and/or a compound thereof.

The oxidation is preferably carried out under acidic conditions. The paraffins which can be oxidated by the process according to the present invention are represented by the general formula

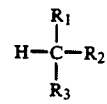

wherein $R_1$ and $R_2$ are selected from the group consisting of linear alkyl containing from 1 to 10 carbon atoms, branched or cyclic alkyl containing from 3 to 10 carbon atoms; or $R_1$ and $R_2$ can jointly constitute a ring-closed divalent radical around the carbon atom. $R_1$ and $R_2$ can be either equal to, or different from, each other, and can also contain such functional groups as halogen, alkoxy, amino, carbonyl, carboxy, carboxy ester and amide;

$R_3$ has the same meaning as of $R_1$ and $R_2$, or is hydrogen.

In the process which constitutes the object of the present invention, a catalyst on the basis of titanium-silicalite and of a noble metal and/or a compound thereof, is used. Such a catalyst may consist of a) a mixture of titanium-silicalite and supported noble metal, e.g., on carbon, or
b) a titanium-silicalite onto which a noble metal or a derivative thereof is deposited, or
c) a titanium-silicalite modified with a noble metal and/or a derivative thereof.

The noble metal is selected from platinum, palladium, iridium, rhutenium and rhodium, and preferably is platinum or palladium. When a noble metal compound is used, said compound can be a salt or a complex of such a noble metal, preferably a platinum or palladium salt or complex, e.g., $PdCl_2$, $PtCl_2$, $H_2PtCl_6$, $Pd(NH_3)_4Cl_2$, $Na_2PtCl_4$, $Na_2PdCl_4$, or the noble metal compound can be $PtO_x$ and $PdO_x$, in which $x=1$ or 2.

The titanium-silicalites are disclosed in UK Patent No. 0 071 071, EPA Publ. Nos. 0 226 257, 0 226 258, 0 266 825 and 0 265 018, and are represented by the following general formula, expressed as molar ratio of oxides (in its calcined and anhydrous form):

$$pHMO_2 \cdot qTiO_2 \cdot SiO_2$$

in which
M is a metal selected from aluminum, gallium and iron, and
p is comprised within the range of from 0 to 0.05, with value zero being also allowed for p, and
q is comprised within the range of from 0.0001 to 0.05, and preferably of from 0.01 to 0.025.

In EPA Public. No. 0 265 018, titanium-silicalites bonded with oligomeric silica are disclosed. The use of said zeolites, both in their pristine and in their bonded form, in the process of hydroxylation of aromatic hydrocarbons (UK Patent No. 2 116 974) and of epoxydation of olefinic compounds (European Patent No. 0 100 119), both in the presence of hydrogen peroxide, has already been disclosed in the past.

In the process according to the present invention, when the catalyst is a mixture of titanium-silicalite and supported noble metal on carbon, such a mixture is accomplished by a mechanical process, and the noble metal is preferably selected from palladium and platinum, in a percentage by weight comprised within the range from 0.5 to 10%, relatively to the support, and in a percentage by weight comprised within the range of from 0.001 to 5%, relatively to titanium-silicalite. Titanium-silicalite can be used as such, and in its form bonded with oligomeric silica.

However, a preferred aspect of the present invention is using as catalyst a titanium-silicalite on which a noble metal or a derivative thereof is deposited. Such a catalyst is novel, and constitutes a second object of the instant invention. It is prepared by treating, in an aqueous solution, titanium-silicalite, as such or in its form bonded with oligomeric silica, with a compound of the noble metal, at a temperature comprised within the range of from 20° to 100° C. The weight ratio of the noble metal to titanium-silicalite is comprised within the range of from 0.001 to 5%. The solvent is then evaporated off and the resulting solid, after being previously dried under vacuum, can be used as catalyst in its pristine form, or can be submitted to a reduction with hydrogen, at a temperature comprised within the range of from 25° C. to 500° C., and under a pressure comprised within the range of from 1 to 20 atm, so as to reduce the metal compound deposited on the zeolite surface, into its metal form. The reduction can be carried out either under dry conditions under a hydrogen stream, or in an autoclave, in a solvent selected from the usual hydrogenation solvents, such as, e.g., water or alcohols, with stirring. In the latter case, the process will be carried out at a lower temperature than the solvent's critical temperature. At the end of the process of reduction in autoclave, the suspension is submitted to centrifugation and the resulting solid residue is washed with distilled water and dried under vacuum.

The noble metal is preferably selected from among platinum and palladium. The sources of palladium and platinum ions which can be used in order to perform the deposition of the metal on the surface of titanium-silicalite are, e.g.: $PdCl_2$, $PtCl_2$, $H_2PtCl_6$, $Pd(NH_3)_4Cl_2$, $Na_2PtCl_4$, and $Na_2PdCl_4$.

The percentage of metal or metal derivative in the thus obtained catalyst is comprised within the range of from 0.001 to 5% by weight.

A second preferred aspect of the present invention is using as catalyst a titanium-silicalite modified with noble metal and/or a derivative thereof, which is dispersed throughout the zeolitic structure. Such a material is novel, and is a further object of the instant invention. It is prepared by reacting under hydrotermal conditions a silicon derivative, a titanium derivative, a derivative of a noble metal, preferably platinum or palladium, and a nitrogenous organic base, with a molar ratio of $SiO_2/TiO_2$ of the reactants comprised within the range of from 10 to 60, a molar ratio of the derivative of the noble metal to $SiO_2$ of the reactants comprised within the range of from 0.0005 to 0.01, a molar ratio of the nitrogenous organic base to $SiO_2$ of the reactants comprised within the range of from 0.1 to 1, and a molar ratio of $H_2O/SiO_2$ of the reactants comprised within the range of from 15 to 100.

The silicon derivative is selected from silica gel, silica sol, and alkyl silicates, among which tetraethylsilicate is preferred; the derivative of titanium is selected from titanium salts and organic derivatives such as, e.g., the alkyltitanates, among which tetraethyltitanate is preferred; the nitrogenous organic base preferably is tetrapropilammonium hydroxide; the platinum or palladium derivative is selected from: $PdCl_2$, $PtCl_2$, $H_2PtCl_6$, $Pd(NH_3)_4Cl_2$, $Na_2PtCl_4$, and $Na_2PdCl_4$.

The reactants are caused to react by operating at a temperature comprised within the range of from 100° C. to 200° C., preferably of from 160° C. to 190° C., at a pH value comprised within the range of from 10 to 13, for a time period comprised within the range of from 1 to 72 hours. At the end, the product is discharged from the autoclave, is washed, is dried, and is calcined at a temperature comprised within the range of from 500° C. to 600° C.

The resulting product contains the metal in the form of a compound and, possibly, according to the conditions selected for the calcination step, it may also contain a small percentage of metal in reduced form. Such a product can be used as such as the catalyst for the process according to the present invention, or it can be previously submitted to a reduction with hydrogen, at a temperature comprised within the range of from 25° C. to 500° C., and at a pressure comprised within the range of from 1 to 20 atm, in order to reduce the metal compound into metal.

The reduction can be carried out either under dry conditions, under a flowing hydrogen stream, or in an autoclave, in a solvent selected from among the usual hydrogenation solvents, such as, e.g., water or alcohols, with stirring. In the latter case, the process will be carried out at a lower temperature than critical solvent temperature. At the end of the reduction process in autoclave, the suspension is submitted to centrifugation, and the resulting solid is washed with distilled water and is dried under vacuum.

The so prepared catalyst can contain a percentage by weight of noble metal and/or of a compound thereof comprised within the range of from 0.01 to 2; it shows a powder X-ray diffraction pattern and an I.R. spectrum similar to as disclosed for titanium-silicalite in U.S. Pat. No. 4,410,501. In particular, the X-ray diffraction pattern of the novel catalyst constituted by titanium-silicalite modified with a noble metal also shows the typical diffraction bands of the metal.

The catalyst obtained by depositing the noble metal, or a derivative thereof, onto the surface of titanium-silicalite, or titanium-silicalite modified with metal and-/or a derivative thereof, can be used in the process according to the present invention either alone, or together with an aliquot of titanium-silicalite in its pristine state.

The oxidation process is preferably carried out in an acidic environment, e.g., containing hydrochloric acid, trifluoroacetic acid, sulfuric acid, nitric acid.

Still more preferably, the process is carried out in the presence of hydrochloric acid, at a concentration comprised within the range of from 0.001 to 1 mol/liter.

Some specific examples of paraffinic compounds which can be oxidated according to the method according to the present invention are: propane, n-butane, isobutane, n-octane and n-hexane.

The reaction products from the process according to the present invention are oxygen-containing compounds deriving from the oxidation of substantially one single carbon atom of the paraffinic compound used as the starting compound. Therefore, mono-alcohols or ketones or mixtures thereof are obtained, with extremely good selectivity, depending on the paraffinic compound used as the starting compound.

The practical implementation of the process according to the present invention comprises reacting the reactants, i.e., paraffin, oxygen and hydrogen, preferably in an acidic environment, in the presence of the catalyst on the basis of titanium-silicalite and a noble metal and/or a derivative thereof, or at a temperature comprised within the range of from 0° C. to 100° C., in autoclave. The reaction mixture can be possibly diluted with nitrogen. The molar ratio of nitrogen to oxygen can be comprised within the range of from 0 to 30. The reaction can be carried out in the presence or less of an inert solvent, batchwise or in continuous mode, with the reaction products being separated from the effluent stream, and any not converted reactants being recycled. Suitable solvents for this process can be methanol, t-butil alcohol, acetone, or mixtures thereof with one another or with water. The temperature at which the process is carried out is preferably comprised within the range of from 20° to 50° C.

The molar ratios of paraffin to oxygen and paraffin to hydrogen are comprised within the range of from 0.1 to 10.

The following examples are illustrative of the present invention, but in no case shall they be understood as being limitative thereof.

The examples from 1 to 9 describe the preparation of the catalysts useful in the process according to the present invention.

Examples from 10 to 35 illustrate the process according to the present invention, in which the catalysts disclosed in examples from 1 to 9 are used.

EXAMPLE 1

Preparation of Catalyst 1

1.8 ml of a solution of aqueous hydrochloric acid at 10%, containing 3% of palladium as $PdCl_2$ is added to 50 ml of distilled water. The resulting mixture is neutralized to pH=7 with a diluted aqueous solution of sodium carbonate, and the resulting precipitate is dissolved again with 0.5 ml of acetic acid.

To the solution 4 g of titanium-silicalite, prepared as in example 1 of U.S. Pat. No. 4,410,501, is added, and then the solvent is slowly evaporated under vacuum, with the suspension being kept continuously stirred. A solid is obtained which is dried under vacuum at 45° C., and then is suspended in 10 ml of methanol. The suspension is treated with hydrogen (3 atm) in a glass autoclave, for 3 hours, at a temperature of 60° C., with stirring.

The solid is centrifuged off, is washed with distilled water until chloride ions are no longer detectable, and then is dried at 65° C. under vacuum, for some hours.

EXAMPLE 2

Preparation of Catalyst 2

0.35 ml of a solution of aqueous hydrochloric acid at 10%, containing 3% of palladium as $PdCl_2$ is added to 50 ml of distilled water. The resulting mixture is neutralized to pH=7 with a diluted aqueous solution of sodium carbonate, and the resulting precipitate is dissolved again with 0.5 ml of acetic acid.

To the solution 4 g of titanium-silicalite, prepared as in example 1 of U.S. Pat. No. 4,410,501, is added, and then the solvent is slowly evaporated under vacuum, with the suspension being kept continuously stirred. A solid is obtained, which is kept at 300° C., under a hydrogen stream (p=1 atm), for 2 hours.

The solid is recovered, is washed with distilled water until chloride ions are no longer detectable, and then is dried at 65° C. under vacuum, for some hours.

EXAMPLE 3

Preparation of Catalyst 3

1.8 ml of a solution of aqueous hydrochloric acid at 10%, containing 3% of palladium as $PdCl_2$ is added to 50 ml of distilled water. The resulting mixture is adjusted to pH=11, and the reddish solid which precipitates off is centrifuged off. After being washed with distilled water until chloride ion is no longer detectable, the precipitate is dissolved again with 0.92 ml of HCl 1.2N.

To the solution 4 g of silica-bonded titanium-silicalite, prepared as in example 1 of U.S. Pat. No. 4,701,428, is added, and then the solvent is slowly evaporated under vacuum, with the suspension being kept continuously stirred. A solid is obtained which is dried under vacuum at 40° C.

EXAMPLE 4

Preparation of Catalyst 4

0.1 ml of an aqueous solution containing 25% of platinum as $H_2PtCl_6$ is diluted with 10 ml of water. To the solution 4 g of titanium-silicalite bonded with silica, prepared as disclosed in example 1 of U.S. Pat. No.

4,701,428 is added, and the solvent is slowly evaporated off under vacuum. The residue is treated with hydrogen under the atmospheric pressure for two hours at 300° C., and then is washed with water until choride ion is no longer detected, is washed twice more with distilled water and is dried at 65° C., under vacuum.

EXAMPLE 5

Preparation of Catalyst 5

4 g of titanium-silicalite prepared according to example 1 of U.S. Pat. No. 4,701,428 is added to a solution of 150 mg of $Pd(NH_3)_4Cl_2$ in 10 ml of distilled water. The solvent is slowly evaporated off under vacuum, and the residue is treated with hydrogen under the atmospheric pressure, for 2 hours, at 300° C. After cooling, the solid is washed with distilled water and is dried at 65° C. for some hours.

EXAMPLE 6

Preparation of Catalyst 6

4 g of titanium-silicalite prepared according to example 1 of U.S. Pat. No. 4,701,428 is added to a solution of 30 mg of $Pd(NH_3)_4Cl_2$ in 10 ml of distilled water. The solvent is slowly evaporated off under vacuum, and the residue is treated with hydrogen under the atmospheric pressure, for 2 hours, at 300° C. After cooling, the solid is washed with distilled water and is dried at 65° C. for some hours.

EXAMPLE 7

Preparation of Catalyst 7

100 mg of $Pd(NH_3)_4Cl_2$ is dissolved in 10 ml of distilled water. To the solution 2.5 g of aluminum-titanium-silicalite, prepared according to example 1 of EPA Public. No. 0 226 257, is added, then the resulting suspension is refluxed for 1 hour. The solid is recovered by centrifugation, is washed twice with distilled water, is dried under vacuum, and then is treated with hydrogen at 300° C., under the atmospheric pressure, for 2 hours. The solid is then washed with distilled water until chloride ion is completely disappeared and then the washed solid is dried under vacuum at 65° C.

EXAMPLE 8

Preparation of Catalyst 8

A solution is prepared by dissolving 1.7 g of tetraethyl orthotitanate in 30 g of tetraethyl silicate, and said solution is added, with stirring, to 55 g of a solution at 13.45% by weight of tetrapropylammonium hydroxide. The resulting mixture is heated at 50° C., with stirring, until a clear, single-phase solution is obtained. 32 g of water is added, and the resulting solution is submitted to distillation at 70° C. under a slow stream of flowing nitrogen, with the initial volume of the distilled mixture being continuously replenished with water. The distillation is continued until 80 g of solvent is collected.

A solution is separately prepared by dissolving in 16 g of water, 15.5 g of an aqueous solution of tetrapropylammonium hydroxide at 13.45% and 0.13 g of $PdCl_2$. The resulting solution is added, with stirring, to the previously prepared solution. A mixture is obtained, which has the following molar composition:

0.32 TPAOH, $SiO_2$, 0.05 $TiO_2$, 0.005 $PdCl_2$, 50 $H_2O$.

Said mixture is charged to a steel autoclave and is kept under its autogenous pressure at 180° C., for 15 hours. At the end the autoclave is discharged, and the product, recovered by centrifugation, is repeatedly washed with water, is dried for 1 hour at 120° C., and then is calcined at 550° C. for 5 hours.

The so obtained material is submitted to reduction under a flowing nitrogen stream, at 350° C., for 4 hours. An anhydrous catalyst is thus obtained, which has the following molar composition:

$SiO_2$. 0.019 $TiO_2$. 0.002 Pd

The material obtained in that way is crystalline at X-ray, shows a similar pattern to as disclosed for titanium-silicalite in U.S. Pat. No. 4,410,501, with additionally the reflections typical of metal palladium, and shows an I.R. spectrum with an absorption band at 960 $cm^{-1}$, analogously to has disclosed for titanium-silicalite in U.S. Pat. No. 4,410,501.

EXAMPLE 9

Preparation of Catalyst 9

1.3 g of an aqueous solution containing 4.2% of platinum as $H_2PtCl_6$ is dropwise added to 56.5 g of an aqueous solution of tetrapropylammonium hydroxide at 13.6%. To the resulting solution, a solution, previously prepared, constituted by 32 g of tetraethyl silicate and 1.7 g of tetraethyl titanate, is added with strong stirring.

The resulting single-phase solution is diluted with 60 g of water, and a mixture is obtained, which has the following molar composition:

0.25 TPA-OH. $SiO_2$. 0.05 $TiO_2$. 0.002$H_2PtCl_6$. 40 $H_2O$

This mixture is charged to an autoclave and is allowed to crystallize, without stirring, at 180° C., under its autogenous pressure, for 15 hours. At the end, the product is discharged, is centrifuged off, is washed many times with water, is dried for 1 hour at 120° C., and then is calcined at 550° C. for 5 hours. The so obtained catalyst, in its calcined and anhydrous form, has the following molar composition:

$SiO_2$. 0.023 $TiO_2$. 0.001 Pt in which platinum is contained in the form of a compound.

This catalyst is characterized by powder X-rays diffraction pattern and an I.R. spectrum similar to those shown by titanium-silicalite, as disclosed in U.S. Pat. No. 4,410,501. Some weak reflections, attributable to the presence of traces of metal platinum are observed in X-ray diffraction pattern.

EXAMPLES 10–28

10 ml of methanol, optionally containing hydrochloric acid, 2 ml of n-hexane, a catalyst such as obtained from examples 1–9, possibly a titanium-silicalite in its pristine state, prepared according to example 1 of U.S. Pat. No. 4,410,501, are charged to a steel autoclave of 140 ml of volume, with a teflon lining.

To the autoclave hydrogen, oxygen, and, optionally, nitrogen are then charged in succession, with the suspension being always kept stirred. After the end of the reaction, the residual gases are discharged and analysed by gas-liquid chromatography, using a 2.4 meters long column of 2 mm of diameter, containing molecular sieves of 5A grade, equipped with a conductivity detector. The suspension is then discharged from the autoclave, the catalyst is removed, the resulting solution is neutralized with sodium hydrogen carbonate, and the obtained products are quantified by gas-chromatography by the internal-standard method, using a 2.3 meters long column of 4 mm of diameter, packed with LAC a pressure of 2.8 atm, with stirring, until pressure remains constant. The identity of the products (alcohols and ketones deriving from the oxidation of paraffins in 2-, 3- and 4-positions, according to the substrate type) was confirmed by mass spectrometry.

The results are reported in following table 3.

TABLE 1

| Example No. | Catalyst No. | (g/l) | Titanium-silicalite (g/l) | Time (hrs) | Temp. (°C.) | HCl (m/l) | $O_2$ (atm) | $H_2$ (atm) | $N_2$ (atm) | $O_2$ Conv. % | 3-one ($10^3 \times$ N/L) | 2-one ($10^3 \times$ N/L) | 3-ol ($10^3 \times$ N/L) | 2-ol ($10^3 \times$ N/L) |
|---|---|---|---|---|---|---|---|---|---|---|---|---|---|---|
| 10 | 1 | 12.5 | 16.7 | 20 | 25 | 0.1 | 0.5 | 0.5 | 5.0 | 23 | 0.19 | 0.25 | 2.2 | 5.8 |
| 11 | 1 | 4.6 | 33.8 | 24 | 25 | 0.1 | 4.0 | 8.0 | — | 4 | 0.22 | 2.6 | 7.7 | 19.0 |
| 12 | 2 | 12.5 | 16.7 | 20 | 25 | 0.1 | 0.5 | 0.5 | 5.0 | 36 | 0.81 | 1.6 | 2.5 | 20.0 |
| 13 | 2 | 12.5 | — | 17 | 40 | 0.01 | 1.0 | 8.0 | — | 73 | 0.68 | 5.1 | 10.0 | 21.5 |
| 14 | 2 | 12.5 | 16.7 | 24 | 25 | 0.01 | 1.0 | 8.0 | — | 78 | 1.30 | 6.8 | 10.4 | 21.2 |
| 15 | 2 | 12.5 | 16.7 | 18 | 25 | 0.1 | 1.0 | 8.0 | — | 33 | 0.92 | 3.9 | 9.2 | 19.0 |
| 16 | 3 | 12.5 | — | 19 | 25 | — | 0.5 | 0.5 | 8.0 | 63 | 0.17 | 1.3 | 4.9 | 15.3 |
| 17 | 4 | 12.5 | — | 19 | 25 | 0.1 | 0.5 | 0.5 | 5.0 | 66 | 0.42 | 0.42 | 1.9 | 4.3 |
| 18 | 5 | 4.2 | 33.3 | 3.5 | 22 | 0.1 | 4.0 | 8.0 | — | 20 | 2.0 | 7.5 | 13.6 | 29.4 |
| 19 | 5 | 12.5 | — | 2.5 | 22 | 0.1 | 4.0 | 8.0 | — | 58 | 12.0 | 7.6 | 13.1 | 26.8 |
| 20 | 6 | 12.5 | — | 24 | 25 | 0.1 | 0.5 | 0.5 | 5.0 | 33 | 0.83 | 1.3 | 4.4 | 6.9 |
| 21 | 6 | 12.5 | — | 19 | 25 | 0.01 | 0.5 | 4.0 | — | 76 | 0.63 | 2.5 | 7.7 | 16.8 |
| 22 | 7 | 12.5 | — | 21 | 25 | 0.1 | 0.5 | 0.5 | 5.0 | 69 | 2.1 | 3.6 | 5.9 | 13.5 |
| 23 | 5% Pd/C | 2.0 | 25 | 3.5 | 25 | 0.1 | 0.5 | 4.5 | — | 100 | 0.13 | 0.65 | 8.2 | 17.1 |
| 24 | 5% Pd/C | 2.0 | 25 | 24 | 20 | 0.1 | 0.5 | 0.5 | 5.0 | 40 | 0.40 | 1.7 | 6.6 | 16.8 |
| 25 | 8 | 12.5 | — | 23 | 20 | 0.1 | 2.0 | 10.0 | — | 17 | 0.97 | 6.3 | 2.5 | 3.2 |
| 26 | 9 | 16.4 | — | 5 | 30 | 0.1 | 0.75 | 0.75 | 4.5 | 37 | 0.38 | 15.2 | 10.0 | 18.9 |
| 27 | 2 | 12.5 | — | 19 | 26 | — | 0.5 | 0.5 | 5.0 | 90 | — | 1.3 | 3.2 | 8.8 |
| 28 | 6 | 12.5 | — | 19 | 26 | — | 0.5 | 0.5 | 5.0 | 90 | 0.3 | 2.7 | 2.6 | 6.1 |

TABLE 2

| Example No. | Catalyst No. | (g/l) | Solvent | Time (hrs) | Temp. (°C.) | Acid (m/l) | $O_2$ (atm) | $H_2$ (atm) | $N_2$ (atm) | $O_2$ Conv. % | 3-one ($10^3 \times$ N/L) | 2-one ($10^3 \times$ N/L) | 3-ol ($10^3 \times$ N/L) | 2-ol ($10^3 \times$ N/L) |
|---|---|---|---|---|---|---|---|---|---|---|---|---|---|---|
| 29 | 6 | 12.5 | $CH_3OH$ | 19 | 27 | $CF_3COOH$ (0.01) | 0.5 | 0.5 | 5.0 | 30 | 0.7 | 2.4 | 1.2 | 2.1 |
| 30 | 1 | 12.5 | acetone/$H_2O$ (80:20 v:v) | 17 | 28 | HCl (0.1) | 0.5 | 0.5 | 5.0 | 43 | traces | 3.0 | 1.6 | 1.0 |

TABLE 3

| Example No. | Catalyst No. | (g/l) | Solvent | Time (hrs) | Temp. (°C.) | HCl (N/L) | $O_2$ (atm) | $H_2$ (atm) | $N_2$ (atm) | $O_2$ Conv. % | 3-one, 4-one ($10^3 \times$ N/L) | 2-one ($10^3 \times$ N/L) | 3-ol, 4-ol ($10^3 \times$ N/L) | 2-ol ($10^3 \times$ N/L) |
|---|---|---|---|---|---|---|---|---|---|---|---|---|---|---|
| 31 | 1 | 12.5 | isobutane | 17 | 29 | 0.1 | 0.5 | 0.5 | — | 26 | — | — | — | 4.0 |
| 32 | 2 | 12.5 | octane | 21 | 25 | 0.1 | 1.0 | 8.0 | — | 79 | traces | 17.3 | 4.1 | 9.4 |
| 33 | 6 | 12.5 | butane | 17 | 27 | 0.1 | 0.5 | 0.5 | 2.2 | 33 | — | — | — | 3.6 |
| 34 | 2 | 12.5 | octane | 17 | 30 | 0.1 | 1.0 | 8.0 | — | 52 | traces | 0.81 | 4.1 | 9.2 |
| 35 | 3 | 12.5 | octane | 19 | 30 | — | 0.5 | 0.5 | 5.0 | 63 | traces | 23.1 | 6.9 | 14.1 |

728 15%, and a FID detector. The identity of the products: 2-hexanone (2-one), 3-hexanone (3-one), 2-hexanol (2-ol) and 3-hexanol (3-ol), was confirmed by mass spectrometry.

The results are reported in table 1.

EXAMPLES 29–30

10 ml of an acid-containing solvent, 2 ml of hexane, the catalyst, hydrogen, oxygen and nitrogen are charged to the autoclave by such modalities as disclosed above. The results obtained are reported in table 2.

EXAMPLES 31–35

By the same procedures as of the preceding examples, 10 ml of methanol possibly containing hydrochloric acid, the catalyst, the paraffin, hydrogen, oxygen and nitrogen are charged to the autoclave.

In particular, octane is added in the liquid state (2 ml), whilst butane and isobutane are charged as gases, under

We claim:

1. Process for the oxidation of paraffinic compounds into their corresponding alcoholic and/or ketonic derivatives, with a mixture of oxygen and hydrogen, by using a catalyst based on titaniumsilicalite and a noble metal and/or a compound thereof, which paraffinic compounds have the general formula

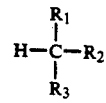

wherein $R_1$ and $R_2$ can be the same, or different from each other, and are selected from the group consisting of linear alkyl containing from 1 to 10 carbon atoms, branched or cyclic alkyl containing from 3 to 10 carbon atoms; or R₁ and R₂ can jointly constitute a ring-closed divalent radical around the carbon atom, or contain such functional groups as halogen, alkoxy, amino, carbonyl, carboxy, carboxyester and amide;
and wherein $R_3$ has the same meaning as of $R_1$ and $R_2$, or is hydrogen.

2. Process according to claim 1, characterized in that said process is carried out in an acidic medium, owing to the presence of a mineral or organic acid.

3. Process according to claim 1, in which the noble metal is selected from platinum, palladium, rhodium, ruthenium and iridium.

4. Process according to claim 3, in which the noble metal is selected from platinum and palladium.

5. Process according to claim 1, in which the noble metal derivative is selected from $PdCl_2$, $PtCl_2$, $H_2PtCl_6$, $Pd(NH_3)_4Cl_2$, $Na_2PtCl_4$, $Na_2PdCl_4$, $PtO_x$ and $PdO_x$, in which x=1 or 2.

6. Process according to claim 1, characterized in that the titanium-silicalite has the following general formula

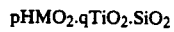

in which

M is a metal selected from aluminum, gallium and iron, and p is comprised within the range of from 0 to 0.05, with the value zero being also allowed for p, and q is comprised within the range of from 0.0001 to 0.05, and preferably of from 0.01 to 0.025, with the $H^+$ ion of $HMO_2$ being possibly, at least partially, replaced by cations.

7. Process according to claim 1, characterized in that the catalyst is a mixture of a titanium-silicalite and a noble metal supported on carbon.

8. Process according to claim 7, in which the noble metal is contained in a percentage by weight comprised within the range of from 0.5 to 10% relatively to carbon, and in a percentage by weight comprised within the range of from 0.001 to 5% by weight, relatively to titanium-silicalite.

9. Process according to claim 1, characterized in that the catalyst is a titanium-silicalite on which a noble metal or a derivative thereof has been deposited.

10. Process according to claim 9, in which the catalyst contains the noble metal or a derivative thereof in a percentage by weight comprised within the range of from 0.001 to 5%.

11. Process according to claim 1, characterized in that the catalyst is a titanium-silicalite in which a noble metal and/or a derivative thereof is dispersed.

12. Process according to claim 11, in which the catalyst contains the noble metal and/or the derivative thereof in a percentage by weight comprised within the range of from 0.01 to 2%.

13. Process according to claim 1, characterized in that as the catalyst a mixture is used, which is formed by a titanium-silicalite as such, and by a titanium-silicalite on which a noble metal or a derivative thereof has been deposited.

14. Process according to claim 1, characterized in that as the catalyst a mixture of titanium-silicalite in its pristine state, and titanium-silicalite in which a noble metal and/or a derivative thereof is dispersed, is used.

15. Process according to claim 1, in which titanium-silicalite is bonded with oligomeric silica.

16. Process according to claim 1, characterized in that the paraffinic compounds which can be oxidated are selected from propane, n-butane, isobutane, n-hexane, n-octane.

17. Process according to claim 1, characterized in that the oxidation of the pataffinic compound leads to the production of mono-alcohols and/or mono-ketones, or mixtures thereof.

18. Process according to claim 2, in which the acid is selected from among hydrochloric acid, trifluoroacetic acid, sulfuric acid and nitric acid.

19. Process according to claim 18, in which the acid is hydrochloric acid.

20. Process according to claim 19, in which hydrochloric acid is used in a concentration comprised within the range of from 0.001 to 1 mol/liter.

21. Process according to claim 1, characterized in that the oxidation is carried out at a temperature comprised within the range of from 0° C. to 100° C.

22. Process according to claim 21, characterized in that the oxidation is carried out at a temperature comprised within the range of from 20° C. to 50° C.

23. Process according to claim 1, characterized in that the oxidation is carried out in the presence of a solvent selected from methanol, t-butyl alcohol, acetone and mixtures thereof with one another or with water.

24. Process according to claim 1, characterized in that the molar ratios of paraffin to oxygen and paraffin to hydrogen are selected within the range of from 0.1 to 10.

25. Process according to claim 1, in which the mixture of oxygen and hydrogen is diluted with nitrogen, and the molar ratio of nitrogen to oxygen is lower than, or equal to, 30.

* * * * *